US00PP13354P2

(12) United States Plant Patent
Heims

(10) Patent No.: US PP13,354 P2
(45) Date of Patent: Dec. 17, 2002

(54) *VERONICA PROSTRATA* PLANT NAMED 'AZTEC GOLD'

(75) Inventor: Dan M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 59 days.

(21) Appl. No.: 09/671,979

(22) Filed: Sep. 27, 2000

(51) Int. Cl.[7] ..... A01H 5/00
(52) U.S. Cl. ..... Plt./251
(58) Field of Search ..... Plt./251

*Primary Examiner*—Bruce R. Campell
*Assistant Examiner*—Anne Marie Grünberg
(74) *Attorney, Agent, or Firm*—Klarquist Sparkman, LLP

(57) ABSTRACT

A new and distinct cultivar of *Veronica prostrata* plant characterized by a unique combination of gold foliage, violet-blue flowers, and sun tolerance.

2 Drawing Sheets

The present invention relates to a new and distinct discovery of *Veronica prostrata*, of the family Scrophulariaceae, which originated as a naturally occurring gold seedling of *Veronica prostrata* (unpatented) found by the applicant, and is given the cultivar name 'Aztec Gold'. The other *Veronica prostrata* seedlings from the sowing had the green foliage typical of the species, rather than the gold foliage that distinguishes this new cultivar.

This new *Veronica prostrata* variety has been reproduced only by asexual propagation (cuttings). Each of the progeny exhibits identical characteristics to the original plant.

This plant is characterized by the following:

1. Gold foliage.
2. Violet-blue flowers.
3. Tolerates full sun.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIGS. 1 and 2 depict the plant as true to type as is photographically possible.

DETAILED PLANT DESCRIPTION

Figure 1:
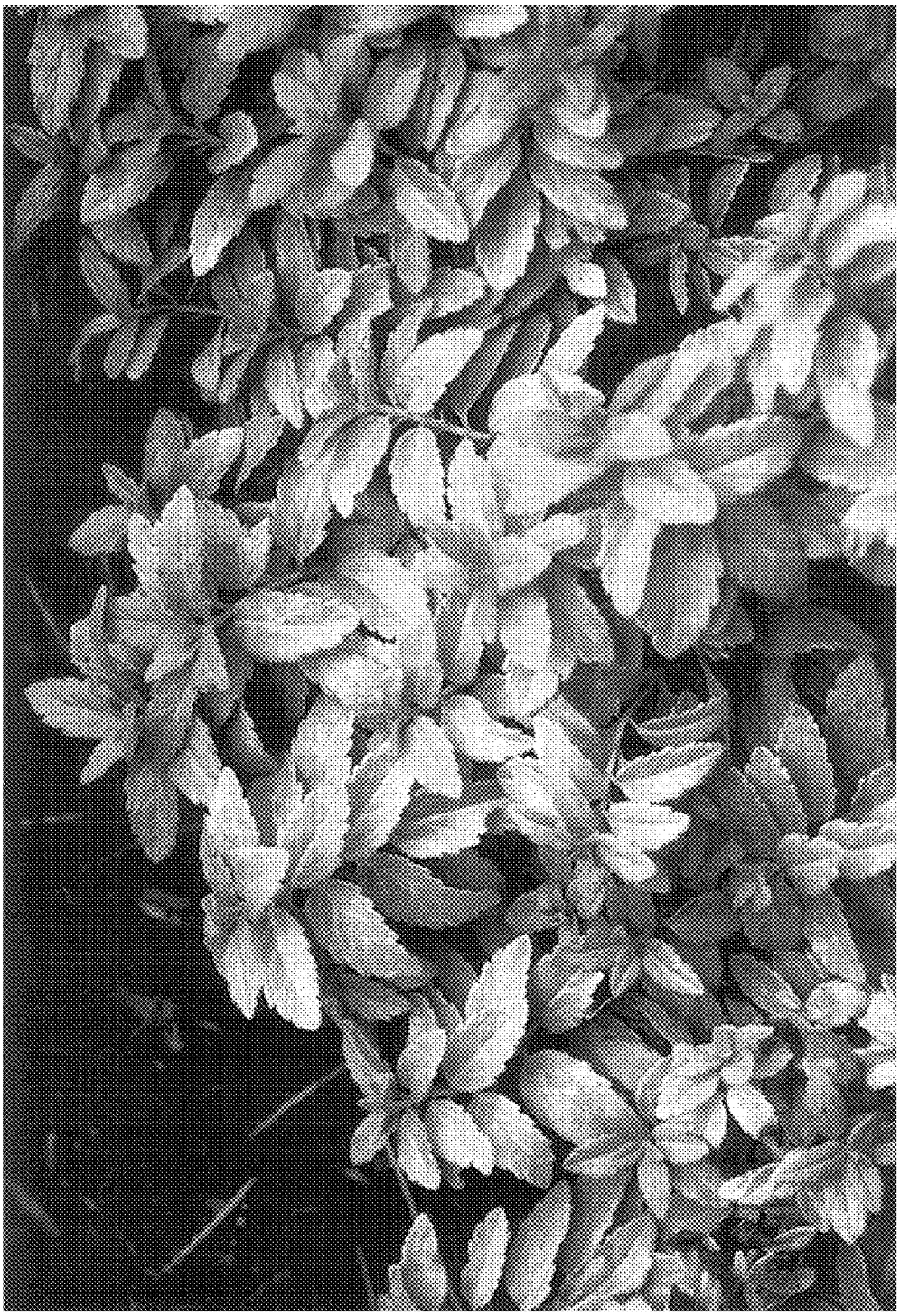
FIG. 1 shows Veronica 'Aztec Gold' foliage over bark dust in spring in Canby, Oreg.
Figure 2:
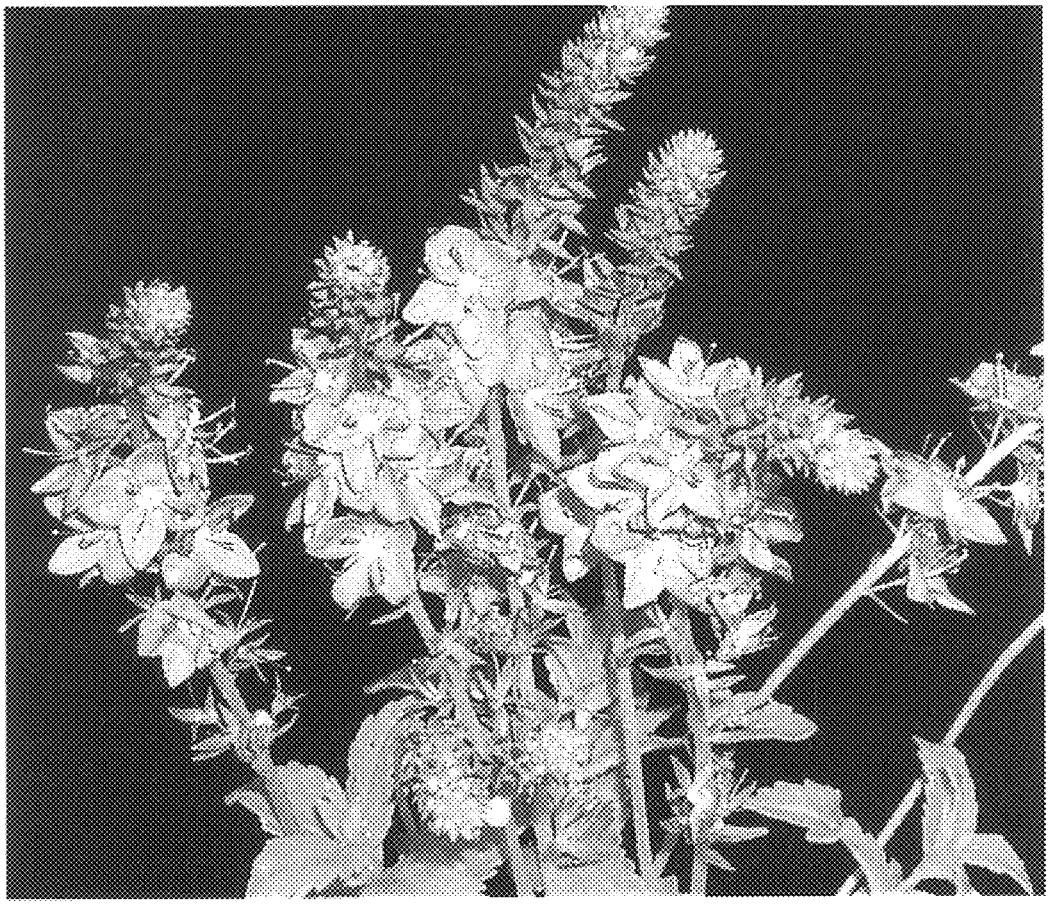
FIG. 2 shows a close-up image of Veronica 'Aztec Gold' flowers.

The following is a detailed description of the new *Veronica prostrata* selection based on observations of one and a half year old specimens grown in the garden in Canby, Oreg. The color descriptions are all based on The Royal Horticultural Society Colour Chart.

Botanical classification: *Veronica prostrata.*
Cultivar name: 'Aztec Gold'.
Plant size (1.5-year-old plants grown in Canby, Oreg.):
- *Foliage height.*—12 cm.
- *Flowering height.*—15–18 cm.
- *Width.*—To 65 cm.

Plant habit: Prostrate.
Hardiness: USDA zone 3.
Foliage:
- *Type.*—Simple. Evergreen.
- *Shape.*—Linear oblong to ovate.
- *Length.*—3–5 cm.
- *Width.*—1.2–2.5 cm.
- *Petiole length.*—2 mm.
- *Margins.*—Serrate.
- *Apex.*—Broadly acute.
- *Base.*—Obtuse.
- *Leaf texture.*—Puberulent.
- *Leaf arrangement.*—Opposite.
- *Venation.*—Pinnate-reticulate.

Flower bud:
- *Size.*—12 mm long and 5 mm wide.

Flower:
- *Type.*—Perfect. Complete.
- *Shape.*—Saucer-shaped.
- *Petal size.*—10–12 mm from petal tip to petal tip.
- *Petal count.*—4, rarely 5.
- *Sepal count.*—4.
- *Ovary position.*—Superior.
- *Carpel number.*—2.
- *Style length.*—10 mm.
- *Stamen number.*—2.
- *Stamen size.*—12 mm. long.
- *Inflorescence type.*—Raceme.
- *Flower number per inflorescence.*—25–45 with 5–15 in full bloom.
- *Bracts.*—8 mm long, below each flower, visible when flowers are buds and very obvious at the tip of the young inflorescence where the are concentrated before the inflorescence expands.
- *Peduncle width.*—1–2 mm.
- *Peduncle texture.*—Puberulent.
- *Peduncle length.*—10–22 cm.
- *Bloom period.*—May to July.
- *Lastingness of the blooms.*—Each flower lasts 5 days if the weather is cool, less if hot.
- *Fragrance.*—None.

Fertility: Undetermined.
Disease: None observed on plants grown commercially in Canby, Oreg.

Color Characteristics

Folige:

*Upper surface.*—New leaves are Light Green, 146B Yellow-Green Group, turning Gold, 17C Yellow-Orange Group, with sun exposure. In low light (winter or shaded) the color is light green, 146B Yellow-Green Group. A leaf may be tow-toned if shaded in part. The gold color may fade on older leaves or in winter to 19A Yellow-Orange Group.

*Lower surface.*—Gold color ranges from 17C to D to 19A Yellow-Orange Group and Light Green color is 146C Yellow-Green Group. The color patterning on the lower leaf surfaces match the upper leaf surfaces.

Flower:

*Bud.*—Violet, 93B Violet Blue Group.

*Flower.*—Overall violet blue, 91A Violet-Blue Group, with darker veins, 92A Violet-Blue Group, and a lighter center, 69D Red Purple Group.

*Sepal.*—144A Yellow-Green Group.

*Anther.*—202A Black Group with pollen that ranges from 158A Yellow-White Group to 161A Greyed-Yellow Group.

*Style.*—92A Violet-Blue Group.

*Filaments.*—91A Violet-Blue Group.

Bracts: Gold, 17C Yellow-Orange Group, when young, expanding to yellow green, 145A Yellow-Green Group.

Peduncle: Light green ranging from 144C to D Yellow-Green Group.

DESCRIPTION OF PARENT PLANTS

The instant plant resulted from a discovery made by the applicant of a gold *Veronica prostrata* seedling. *Veronica prostrata*, as described in *A–Z Encyclopedia of Garden Plants* by the American Horticultural Society (1996), is a "Mat-forming perennial with short, branched, decumbent stems bearing linear-oblong to ovate, toothed, bright to mid-green leaves, 0.8–2.5 cm long. In early summer, produces erect, terminal, spike-like racemes, 2–4 cm long, of saucer-shaped, pale to deep blue flowers." The instant plant differs from *Veronica prostrata* in having brilliant gold foliage. Of the plants, known to the applicant, that are available in the horticulture industry, the instant plant most resembles *Veronica prostrata* 'Trehane' (unpatented). Veronica 'Trehane' has gold mat-forming foliage, deep blue flowers, and perfers partial shade. Veronica 'Trehane' suffers from leaf scorch when grown in full sun. Veronica 'Aztec Gold', however, tolerates full sun and has violet-blue flowers.

I claim:

1. A new and distinct variety of *Veronica prostrata* plant substantially as shown and described, characterized by a unique combination of gold foliage, violet-blue flowers, and sun tolerance.

* * * * *